United States Patent [19]

Wuest et al.

[11] Patent Number: 5,138,046
[45] Date of Patent: Aug. 11, 1992

[54] PROCESS FOR PREPARING ALKYLGLUCOSIDE COMPOUNDS FROM OLIGO- AND/OR POLYSACCHARIDES

[75] Inventors: Willi Wuest, Ratingen; Rainer Eskuchen, Duesseldorf-Benrath; Josef Wollmann, Herzogenrath; Karlheinz Hill, Erkrath; Manfred Biermann, Muelheim, all of Fed. Rep. of Germany

[73] Assignee: Henkel Kommanditgesellschaft auf Aktien, Duesseldorf, Fed. Rep. of Germany

[21] Appl. No.: 656,041

[22] PCT Filed: Aug. 4, 1989

[86] PCT No.: PCT/EP89/00923
§ 371 Date: May 13, 1991
§ 102(e) Date: May 13, 1991

[87] PCT Pub. No.: WO90/01489
PCT Pub. Date: Feb. 22, 1990

[30] Foreign Application Priority Data

Aug. 13, 1988 [DE]  Fed. Rep. of Germany ....... 3827534

[51] Int. Cl.$^5$ .................... C07H 15/04; C07H 3/06; C08B 30/00

[52] U.S. Cl. .................... 536/18.6; 536/18.5; 536/120; 536/124

[58] Field of Search .............. 536/18.5, 18.6, 120, 536/124

[56] References Cited

U.S. PATENT DOCUMENTS

| | | | |
|---|---|---|---|
| 2,390,507 | 12/1945 | Cantor | 536/18.6 |
| 3,219,656 | 11/1965 | Boettner | 536/18.6 |
| 4,721,780 | 1/1988 | McDaniel, Jr. et al. | 536/18.6 |
| 4,889,925 | 12/1989 | Schmid et al. | 536/18.6 |
| 4,990,605 | 2/1991 | Lueders | 536/18.6 |

FOREIGN PATENT DOCUMENTS

| | | |
|---|---|---|
| 35589 | 9/1981 | European Pat. Off. . |
| 99183 | 1/1984 | European Pat. Off. . |
| 2017240 | 5/1970 | France . |

*Primary Examiner*—Ronald W. Griffin
*Attorney, Agent, or Firm*—Ernest G. Szoke; Wayne C. Jaeschke; Daniel S. Ortiz

[57] ABSTRACT

Surface active alkylglucosides are prepared in a 2-step process from starch or starch degradation products such as polyglucose or glucose syrup, the first step consisting of reaction with a short chained alcohol, particularly butanol, while the second step comprises transacetalization with the longer chained $C_{8-22}$, more particularly $C_{12-18}$, alcohol, with fatty alcohols of natural origin preferably being used.

25 Claims, No Drawings

PROCESS FOR PREPARING ALKYLGLUCOSIDE COMPOUNDS FROM OLIGO- AND/OR POLYSACCHARIDES

The preparation of reaction products containing surface active alkylglucoside compounds has been described in numerous publications. As is well known, alkylglucosides are acetals obtained from sugars and monofunctional alcohols. The surfactant components are, more particularly, overwhelmingly monoglucoside containing reaction products of monofunctional aliphatic alcohols having 8 to 22, more particularly 12 to 18 carbon atoms and glucose as the monosaccharide. Depending on the method of preparation the corresponding reaction mixtures contain minor amounts of corresponding acetals which contain the residue of the longer-chained monofunctional alcohol bound to oligosaccharide residues. The term alkylglucoside is here intended to refer to the alkylmonoglucosides as well as alkyloligo- or alkylpolyglucosides, as well as corresponding alkenyl compounds, unless the particular structural differences are expressly mentioned.

The surface active alkylglucosides with $C_{8-22}$, especially $C_{12-18}$, alkyl or alkenyl groups belong to the category of non-ionic surfactants. Their molecular component which can be traced to the longer chained monofunctional alcohols leads back to corresponding alcohols of natural and/or synthetic origin. The saccharide starting material which is of most value in practice consists of the polyanhydroglucose compounds which are abundantly available in nature, the individual glucose units of these are present in an alpha-glucosidic linkage. The most important starting material of natural origin of this kind is starch, which is produced worldwide by crop plants of all kinds, such as potatoes, maize, tapioca, rice, wheat and the like. Powdered starches and their partial degradation products, for example in the form of a corresponding, usually highly concentrated glucose syrup, are available as comparatively cheap starting materials.

Within the framework of the numerous attempts to produce alkylglucoside compounds useful for washing or cleansing, the problems of this category of substance have become known to those skilled in the art. It is difficult to obtain alkylmonoglucosides of this kind with the degree of purity required in practice, i.e. with light colours and a high colour constancy in an alkaline medium. The high susceptibility of the polyanhydroglucose starting material to the high temperatures and pressures required during processing under the influence of catalysts has hitherto stood in the way of the discovery of a method in which alkylglucoside-containing reaction products can be prepared, for example from powdered starch, on an industrial scale in a single operation.

The relevant literature on the preparation of the desired alkylglucosides with a detergent action is concerned particularly with two auxiliary elements which are used in varying ways in the course of different kinds of synthesis. First of all, it is proposed that the polyanhydroglucose components should not be used as they are, but that this starting material of natural origin should first be degraded into the monosaccharide, i.e. glucose. The glucose can then be subjected to acetalisation as an anhydrous material or as a glucose hydrate.

The second auxiliary method used in practice makes use of the fact that lower monofunctional alcohols, particularly those with a carbon atom content of up to 6, and particularly $C_{3-5}$, lead comparatively easily to the desired acetalisation of the monosaccharide. The acetals of the monosaccharide thus formed, however, have only inadequate surfactant properties. They are converted by re-acetalisation with the longer chained alcohols in the range from $C_{12-18}$ into the desired alkylglucoside reaction products having surface active properties. Even this apparently relatively easy method of manufacture involves, in practice, numerous restrictive problems of the kind mentioned above. Hitherto, the recovery of light coloured, colour-fast alkylglucosides, particularly those which are colour-fast in an alkaline medium, has involved such high expenditure that for reasons of cost alone this class of surfactant components with a detergent or cleansing action has not achieved any practical application worth mentioning. From the extensive prior art, just a few examples may be mentioned: U.S. Pat. No. 3219656 describes the preparation of long chained alkylglucoside mixtures by means of a series of successive alcohol exchange reactions. The process starts with glucose. U.S. Pat. No. 3547828 describes the preparation of a ternary mixture of alkyloligoglucosides, alkylmonoglucosides and the corresponding $C_{11}$–$C_{32}$ alkanols by the transacetalisation process with butanol. Here again, glucose is initially reacted with butanol, using an acid catalyst, to form alkylglucoside and the alkylglucoside is subsequently subjected to transacetalisation. U.S. Pat. No. 3598865 describes the conversion of glucose or methylglucoside into long chained glucoside compounds in the presence of primary and secondary alcohols with 3-5 carbon atoms.

U.S. Pat. No. 4223129 describes the conversion of starch with a natural moisture content into methylglucoside without any preliminary drying of the starch. European Patent Application 0099183 describes the conversion of saccharides, particularly polysaccharides such as starch, with alcohols having at least 3 carbon atoms into glucoside mixtures. The reaction is supposed to be carried out in the presence of at least 2 mol of water for each molar saccharide unit in the presence, in particular, of acid catalysts. Preferably, the liquid phase used to disperse the polysaccharide compound additionally contains an alcohol-soluble organic auxiliary solvent. Examples of particularly suitable alcohols for forming the alkylglucoside compounds are the alkanols with 3-6 carbon atoms, and particularly those with 3 or 4 carbon atoms, butanol being of particular interest. The lower alkylglucosides formed in this way can, according to the information in this publication, be used as intermediate compounds in the preparation of surface active alkylglucoside compounds, although no further information is given on the next reaction step.

German Patent Application P3723826.4 describes a multi-step process for preparing surface active alkylglucosides, in which glucose is first reacted with butanol to form an intermediate reaction product and this is then reacetalised with higher alcohols, predominantly having 12 to 18 carbon atoms.

The invention is based on the objective of converting the polyglucoside compounds which are cheaply available as natural raw materials, of the nature of starches or the partial degradation products thereof, into the desired alkylglucoside compounds with surface active properties in a single operation, without the need to isolate any intermediate stages Admittedly, the process according to the invention does itself consist of several steps but it is designed so that it leads from the polysaccharide directly to the alkylglucoside with a detergent or cleaning action as a self contained operational unit, preferably with at least some of the reactants which are need in the meantime being circulated. Alkylglucosidic reaction products are obtained which meet the required standards concerning lightness of colour, colour fastness and alkali resistance. The cost involved in the preparation according to the invention is kept within limits by the measures according to the invention so that it is now on a par with the prices of alternative surfactants used in practice.

The invention therefore relates to a process for preparing reaction products containing surface active alkylglucoside compounds with a predominant content of alkylmonoglucosides from oligo- and/or polysaccharides, particularly starch or partial starch degradation products, and longer-chained monofunctional alcohols with the inclusion of the intermediate formation of low alkylglucosides and the transacetalisation thereof with the longer-chained monofunctional alcohols. The process according to the invention is characterised in that
a) the saccharide starting material is reacted, with acidic catalysis, with such quantities of a water/low alkanol mixture which is in a single phase at the operating temperature, at temperatures above 100° C. and elevated pressures, so that throughout the entire reaction the stirability and flowability of the reaction mixture are maintained and the reaction is continued until a liquid, virtually clear single-phase first reaction product is obtained, after which
b) this first reaction product, optionally after preliminary treatment with an adsorbant to brighten its colour, e.g. activated charcoal or ion exchanger, is combined with the longer-chained alcohols preheated to elevated temperatures, again with the formation of a second reaction mixture which is single-phase at the operating temperature in the liquid component throughout the entire reaction, under such reaction conditions of pressure, temperature and rate of addition that the water content introduced is converted into the vapour phase virtually immediately and there is condensed together with the accompanying low alkanol and hence removed from the events of the reaction, after which
c) whilst the single phase nature of the liquid component is maintained, any low alkanol still present therein and/or liberated by transacetalisation is evaporated off and the second reaction product thus formed is, if desired, further purified in a manner known per se, more particularly by neutralisation, elimination of excess longer-chained alcohol and/or bleach.

The process according to the invention thus arrives at the objective set by means of a combination-of process steps which optimally enable one to achieve the desired conversion, on the one hand, and on the other hand yield a reaction mixture which can be further processed in the next process step as the starting material (suitably treated in accordance with the invention) without any problems, so as to obtain the desired end product. The special features and preferred elements of the procedure according to the invention will hereinafter be described in the sequence of the multi-step process.

Suitable glucose starting materials are polysaccharide compounds, particularly those of natural origin, which contain alpha-glucosidically linked polyanhydroglucose units, particularly in a chain of greater or lesser length. The preferred polysaccharide for processing in the process according to the invention is starch of any origin, particularly native starch from potatoes, maize, tapioca, rice, wheat and the like and/or the partial degradation products thereof, which are cheaply available in the form of usually highly concentrated, aqueous, syrupy products as polyglucose or glucose syrup. There is no need for any preliminary treatment of any kind, particularly drying of the starting material, since, on the contrary, the process according to the invention provides for the use of considerable quantities of water as an essential element in the first step. Moreover, the aqueous, syrupy starting materials commercially available generally require the addition of more water in order to make them suitable for the first step of the process according to the invention. In this first step, the saccharide starting material is reacted with such quantities of a water/low alkanol mixture which is single-phased at the process temperature, at temperatures above 100° C. and under elevated pressures in the presence of an acid catalyst, so that the stirability and flowability of the reaction mixture are maintained throughout the reaction. The following points of view should be borne in mind in particular:

When water is used and the conditions according to the invention are applied, the starch particle is subject to effects which are on the one hand desirable, but which on the other hand jeopardise the process. The primary desired effect is the breaking up of the quasi-crystalline tertiary structure of natural starch particles by swelling and glutinisation of the starch molecules under the effect of water. The consequent danger to the process consists in the glutinisation of the starch and hence partial or complete solidification of the reaction mixture during the first step. According to the invention, this danger is overcome by using sufficient quantities of the aqueous, alcoholic liquid phase so that the stirability and flowability of the reaction mixture is ensured at the processing temperatures prevailing throughout the entire reaction Numerically established details of this process step will be given hereinafter. The operational reliability of this first step is further improved by using the water in the form of a water/low alkanol mixture which is single-phase at the process temperature. The water content of this liquid phase initially breaks up the particle structure of the starch particle and presumably leads to at least partial hydrolosis of the polysaccharide towards a monosaccharide. The low alkanol component which is simultaneously present in the homogeneous mixture leads, under the process conditions, to at least partial acetalisation of the glucose or oligo-glucose components formed. Presumably, the solubility of the resulting reaction mixtures in the liquid phase used and hence the mobility of this first reaction mixture are thus improved.

In a preferred embodiment of the invention, at least during substantial parts of this first process step, the liquid reaction material is thoroughly mixed, conventional stirring apparatus for autoclaves (about 200 rpm) being sufficient for this purpose in the laboratory. In the case of mixtures on an industrial scale, in-line mixing elements such as Supraton mixers, for example, are preferably used as highly effective stirring equipment.

The reaction between the selected poly- and/or oligosaccharide water and lower alkanol takes place under the action of acidic catalysis. Both here and in the subsequent process steps, the acid catalysts based on inorganic and/or organic acids which have frequently been described in connection with the preparation of alkylglucosides are suitable. Particularly suitable acid catalysts are sulphonic acids, particularly aromatic sulphonic acids. An outstanding example is p-toluene sulphonic acid.

For the preparation of sufficiently light coloured reaction end products it is important to choose, from the outset, reaction conditions for the multi-step process which allow a comparatively gentle effect everywhere where undesirable dark colouration can be expected under an intensive effect. In this connection it is particularly useful to heat the reaction mixture and obtain the desired temperature level. It may be preferred within the scope of the invention to create comparatively mild process conditions—in spite of the necessary process temperature of above 100° C.— by having the heating of the reaction mixture take place in a circulating partial current outside the main reactor. By using comparatively large heat exchange surfaces in this partial current, it is possible to work with temperatures in the heated medium used which are only slightly above the process temperature and at the same time sufficiently rapid heating of the reaction mixture is ensured. Details of this preferred measure within the procedure according to the invention will be given in the following explanation of the second step of the process.

The monofunctional lower alkanols used in homogeneous mixture with water in this first process step are supposed, in the preferred embodiment of the invention, to form azeotropes with water which make it easier to separate a water/alcohol mixture from the reaction mixture in the reaction which follows. The lower alcohols having 3 to 5, more particularly 3 to 5 carbon atoms are particularly suitable. The representatives which are able to form heterogeneous azeotropes are of particular importance again, i.e. the ones whose azeotrope leads to spontaneous phase separation during condensation. In this way, the water introduced into the process can be circulated out in subsequent reaction steps, whilst at the same time at least the majority of the monofunctional alcohol can be recycled into the process. The butanols are the most important alcohols in the sense of the invention, n-butanol being of particular importance.

Under the process conditions of temperature and pressure applied in the first step of the process according to the invention, within a comparatively short time of about 15 to 30 minutes a reaction mixture is obtained in the form of a liquid, substantially clear single phase first reaction product. The formation of a single phase reaction product of this kind and the retention of the single phase nature of the liquid material used throughout the process as a whole is of major importance in preparing high grade alkylglucoside products of the type desired. The occurrence of phase separation generally causes the reaction to go off course and produce undesirable byproducts which cannot be worked up in subsequent process steps to obtain the desired alkylglucoside. In particular, the colouration of the reaction product is negatively affected. Other problems may lie in the undesirable coating of the interior of the reactor with viscous liquid polyglucose syrups. The single phase quality required according to the invention in the liquid fraction used and finally the formation of a substantially clear single-phased first reaction product prevent problems of this kind (the single phased nature relating to the first reaction product under the reaction conditions).

The saccharide digestion of the first reaction step is preferably carried out at temperatures above 125° C., whilst it is preferable to work in the range from about 135° to 170° C., preferably 140 to 160, and more particularly in the range from about 140° to 150° C. Expediently, this digestion is carried out with at least partial formation of the low alkylglucosides at the inherrent pressure established in the sealed system. In the preferred temperature range this inherrent pressure is approximately in the range from 4 to 10 bar, more particularly 4 to 8 and especially in the range from about 4.5 to 7 bar. Under these process conditions it is possible, for example, to digest native starch powder in the comparatively short reaction time of about 15 to 30 minutes at the operating temperature to obtain the single phase reaction product required according to the invention, which can be used in the subsequent process steps.

In order to prepare the first reaction mixture it is preferable to use water and the monofunctional low alcohol— particularly n-butanol— in substantially equal molar amounts. It is also preferred to use molar ratios of saccharide compound: water in the first reaction mixture in the range from about 1:5 to 12, preferably 1:6 to 12, more particularly about 1:6 to 9, and especially about 1:8. These calculations are based on the saccharide compound used (calculated as anhydroglucose, molecular weight 162) in the anhydrous state, i.e. the quantity of water which is introduced into the reaction by the saccharide starting material also has to be taken into account in the calculation, be it in the form of the natural water content of starches (usually about 12 to 18%), or in the form of the water content of an oligoglucose syrup.

The single phase first reaction product obtained as described may be introduced as it is into the subsequent second process step; however, it may also be at least partially cooled and/or stored in the meantime and/or lightened in colour by the use of adsorbants. The process can be simplified by lowering the temperature of this first reaction mixture to less than 100° C. in order the enable the current of product to be conveyed onwards under normal pressure.

In the subsequent second process step, this first reaction product is combined with the longer chained alcohols preheated to elevated temperatures under specifically selected reaction conditions. In order to obtain a high level of reaction and produce alkylglucoside reaction products of the desired colour and structure, it is important to carry out the combining of the first reaction product with the preheated longer chained alcohols under such conditions of temperature, pressure and rate of addition that the water introduced is converted into vapour almost immediately. The invention thus aims at eliminating the considerable quantities of water from the first process step still present in the second part of the process as rapidly as possible from the reaction, so as to ensure the desired transacetalisation under process conditions which result in high-quality end products.

Of the longer chained alcohols with 8 to 22 carbon atoms, the aliphatic primary $C_{12}$–$C_{18}$ alcohols are particularly important. These are preferably saturated and more particularly straight chained alcohols such as may be obtained by the hydrogenation of native fatty acids on an industrial scale. Typical examples of the higher aliphatic alcohols which may be used in the process according to the invention include the compounds n-dodecyl alcohol, n-tetradecyl alcohol, n-hexadecyl alcohol, n-octadecyl alcohol, eicosyl alcohol, n-octylalcohol, n-decylalcohol, undecyl alcohol, tridecyl alcohol or unsaturated alcohols such as oleyl alcohol and erucyl alcohol. Since the fatty alcohols preferably originate from natural fat sources, mixtures of industrial fatty alcohols may usually be considered as reactants. In addition to true fatty alcohols it is also possible to use branched primary alcohols, such as the so called oxoalcohols, for the reaction. Typical oxoalcohols include, for example, the compounds $C_{12}$–$C_{13}$ alkanol with about 25% of mainly 2-methyl branches (dobanol 23) and the corresponding $C_{9-11}$ alkanol (dobanol 91). A central aim of the process is the preparation of surfactants which can be produced exclusively from replaceable raw materials.

In the preferred embodiment, the longer chained alcohols are pre-heated at least to the process temperature of the second stage of the reaction. Then the first reaction product with a high water content is combined either stepwise or continuously with the hot reactive alcohol phase so that the water introduced leaves the liquid phase almost immediately and goes into the vapour phase. This process step is aided by the concomitant use of lower monofunctional alcohols and particularly n-butanol. The water goes over with this alcohol as an azeotrope. As is well known, n-butanol forms a particularly water-rich heterogeneous azeotrope which, after condensation, leads to the spontaneous separation of an aqueous phase which is removed from the process to the necessary extent whilst the butanol phase forming in the condensate and the residual water can be recycled into the process.

In order to put this process condition into effect to an optimum degree-it may be desirable to feed the aqueous first reaction product directly into the preheated main amount of the higher alcohol and remove the spontaneously released vapour phase from the reaction by condensation. An important condition for trouble-free performance of the process according to the invention is that even in this second process step, throughout the entire course of the reaction, at the process temperature, the single-phase condition of the liquid component is guaranteed. This condition can be achieved and monitored by controlling in particular the rate of addition of the aqueous first reaction product and the temperature. In this step, too, sufficiently intensive mixing of the liquid reaction material may be advantageous.

Considerable amounts of energy have to be supplied to the second reaction step in order to vaporise the water/butanol fractions from the first reaction product.

The specific conditions of heat supply are of particular importance in the production of high quality end products. In a preferred embodiment, when this heat energy is supplied to the second reaction mixture, a very restricted temperature difference $\Delta T$ (delta T) must not be exceeded. $\Delta T$ is calculated as the difference between T (heating medium) and T (second reaction mixture). The absolute value of $\Delta T$ should be not more than 30° C. in the preferred embodiment and preferably not more than 20° C. In practice, particularly good results are obtained if the operation is carried out with a $\Delta T$ in the range from 10° to 20° C.

In order to be able to implement this important condition in spite of the comparatively high demands on the supply of heat to the second step of the reaction, the vapourising energy required is supplied particularly by the heating of a partial current of this reaction mixture circulating outside the main reactor. In this circulating system, a heat exchanger is provided outside the main reactor, of such a size that the large quantities of vapourising energy required can be replaced or supplied almost spontaneously, without exceeding the condition of the maximum for $\Delta T$ which is important according to the invention.

The second reaction step is preferably carried out at temperatures just below the first reaction step, i.e. in the range from 100° to 140° C., whilst temperatures in the range from about 110 to 120 C may be preferred. The course of the reaction in this stage of transacetalisation requires a certain retention time of the reaction material in this stage of the process. First of all the aqueous first reaction product is fed in and the almost immediate expelling of the water content from the second reaction mixture formed is ensured. This is followed by a subsequent reaction phase of increasing transacetalisation, whilst any low alkanol, particularly n-butanol, still present in the reaction mixture and/or released by transacetalisation is evaporated off. This process step can be promoted by step wise or continuous lowering of the pressure in this reaction step. Preferably, every endeavour is made to lower the pressure during this transacetalisation so that the final pressures of this stage of the process are below 100 m bar, preferably below about 50 m bar and in particular in the region of about 10 m bar. The butanol distilled off can in turn be recycled into the process.

The course of the process according to the invention envisages that the longer chained alcohols are present in a substantial excess virtually throughout the entire stage of the process comprising the addition of the first reaction product to the pre-heated longer chained alcohol or alcohol mixture. This greatly favours the formation of the particularly desirable high yields of monoalkylglucoside. For this reason, in the process according to the invention the quantities of alcohol to be used for the transacetalisation can be reduced by comparison with known methods without having a negative effect on the formation of the desired large amounts of monoalkylglucoside. According to the invention it is therefore preferred to use molar ratios of the introduced saccharide compound (based on anhydroglucose) to the longer-chained alcohol in the range from 1:1.5 to 7, preferably 1:2.5 to 7, and more particularly in the range from about 1:3 to 5, in the entire second reaction mixture. This constitutes a major improvement in the process for the step of concentrating the amount of free longer-chained alcohol in the second reaction product, which is usually the next step.

The transacetalisation of the second process step is also carried out under acid catalysis. It may be convenient to increase the amount of acid catalyst transferred with the first reaction product by adding additional catalyst to the second process step. Once again, sulphonic acids in particular and especially aromatic sulphonic acids and more particularly p-toluene sulphonic acid are suitable catalytically active compounds. Longer-chained alcohols or alcohol mixtures of natural and/or synthetic origin, particularly primary alkanols, are suitable as alcohol starting materials for the second step of the reaction. The replaceable fatty alcohol which may be obtained by a reduction of fatty acids of natural origin may be of particular importance. However, corresponding alcohols or alcohol mixtures of synthetic origin such as the oxoalcohols, for example, are equally suitable. The particular chain length of the alcohols or alcohol mixtures used is chosen in accordance with the surfactant properties required of the alkylglucosides.

For broad ranges of applications, chain lengths of $C_{12-18}$ are particularly suitable.

The reaction product obtained from the second step of the reaction is further purified in a manner known per se and worked up as described in detail in the literature mentioned herein before and especially in the above mentioned application P3723826.4.

Accordingly, first of all neutralisation of the acidically catalysed reaction product can be considered. Organic or inorganic basic alkali, alkaline earth metal or aluminium or alkali/aluminium compounds are suitable for this. Preferably, pH values of at least 8, preferably about 9 are obtained. The catalyst may conveniently be neutralised with magnesium compounds in particular, for example, organomagnesium compounds such as magnesium alkoxides or inorganic magnesium compounds such as magnesium oxide or magnesium hydroxide. However, zeolite NaA is a useful neutralising agent, particularly in admixture with calcium hydroxide. By establishing alkaline levels in this neutralisation step, it is possible to ensure the colour stability of the surfactant in the alkaline range during its subsequent processing.

The excess fatty alcohol may be distilled off in known vacuum distillation apparatus which are gentle to the product. It is particularly suitable to use thin layer and/or falling film evaporators.

The end product of the reaction when cooled constitutes a waxy mass which is converted to improve its handling qualities into an aqueous paste with contents of active substance of more than 50%, in a manner known per se. In this form, if necessary, the colour may be additionally corrected and lightened in particular by simply bleaching with hydrogen peroxide or an organic per acid or corresponding per acid salts.

The mixture of substances obtained in the process according to the invention corresponds in composition to the disclosure from the above mentioned German Patent Application P3723826.4, the data of which will be referred to for the sake of simplicity in order to complete the disclosure of the invention.

EXAMPLES

Example 1

Potato starch is processed in the multi-step process according to the invention to obtain a reaction product containing surface active alkylglucoside compounds. The following ingredients are used in the quantities specified:

250 kg of powdered starch (water content 18%), corresponding to 205 kg of starch (anhydrous) plus 45 kg of water.
795 kg of n-butanol
1480 kg of $C_{12/14}$ fatty alcohol (native basis)
135 kg of added water (total water from starch used plus additional water is 180 kg)
7.6 kg of p-toluene sulphonic acid $\times 1$ $H_2O$, of which 5.6 kg are used in the first reactor, the remaining 2.0 kg being added to the second reactor.
4.2 kg of magnesium oxide for neutralisation The ratios of quantities of the starting materials correspond to the following molar ratios, each based on 1 mol of anhydrous potato starch (calculated as anhydroglucose):

8 mol of water, 8.5 mol of butanol, 6 mol of $C_{12/14}$ fatty alcohol, $3.16 \times 10^{-2}$ mol of p-toluene sulphonic acid and $8.22 \times 10^{-2}$ z mol of magnesium oxide The reaction is carried out in detail as follows:

butanol and water are placed in a first reactor. This first reactor is equipped as a stirrer reactor with a volume of 2.5 $m^3$, with a 3-stage stirring mechanism with expeller blades and additionally containing a Supraton Inline mixer with a capacity of 2 $m^3/h$. This first reaction container also has an external liquid circuit with a heat exchanger.

The butanol/water mixture placed in the reactor is pumped round using the Inline mixer. The powdered starch and the first fraction of the acid catalyst (5.6 kg of p-toluene sulphonic acid) are added to the butanol/water mixture. The reaction mixture is heated to the reaction temperature of 140° to 145° C. under inherent pressure, using the heatable circulating line for supplying heat. The inherent pressure established in the closed system ranges from 4.3 to 4.7 bar. After a reaction time of 0.33 hours at a reaction temperature of 140° to 145° C., the reaction mixture is cooled to 70° to 80° C.

In a second reaction container are the $C_{12/14}$ fatty alcohol and additional 2 kg of p-toluene sulphonic acid. The second reaction container is equipped as a stirrer reactor with a volume of 3.2 $m^3$ and it is fitted with a rectifying column. In addition, an external liquid circuit is provided which comprises a circulating pump with a delivery of 20 $m^3/h$ and a heat exchanger in the form of a tube bundle with an exchange surface of 20 $m^2$.

The mixture of fatty alcohol and catalyst is pumped through the external circuit and heated to a reaction temperature of 115° to 118° C. A pressure of 700 m bar is applied to the reactor. As soon as the prescribed reaction temperature and reaction pressure have been established, the reaction mixture is metered from the first reactor into the second reactor continuously within 2 hours.

Butanol and water are continuously removed from the reaction mixture as rapidly as possible. The vaporising energy required for this is supplied via the heat exchanger of the external liquid circuit at a $\Delta T$ value not exceeding 20° C.

The condensate obtained from the vapour phase removed separates into a heavy phase rich in water (92.3% water, 7.7% butanol) and a supernatant butanol-rich phase. 45 kg of water which has entered the reaction mixture as the natural water content of the starch are removed from the system as the heavy phase. The remaining water and the butanol are collected in a storage container and recycled into the process for the next batch.

After the end of the metering of the reaction mixture from the first reactor into the second reactor butanol remaining or liberated in transacetalization is now removed as fully as possible from the second reactor. For this purpose, the pressure in the reactor is reduced step wise to a final pressure of about 10 m bar. The time taken for this is about 1 hour.

After the transacetalisation has ended, the reaction mixture is cooled to 90° C. and neutralised with the magnesium oxide. Subsequently, in a manner known per se, the excess $C_{12/14}$ fatty alcohol is separated off by distillation, the product thus obtained is worked up to an aqueous paste with a content of active substance of about 60% and bleached by the addition of hydrogen peroxide.

In subsequent reaction mixtures, whilst the molar ratios described are retained, the potato starch is replaced first of all by bleached corn starch and then, in a subsequent mixture, by unbleached corn starch, the water content being 11 to 13% in each case. Even these natural starch materials can be worked up without any problems and result in reaction products of comparable quality containing predominantly monoalkylglucosides.

EXAMPLE 1A

The same procedure was used as described above, whilst in the first reaction step the inherent pressure was in the range from 5.0 to 5.5 bar.

EXAMPLE 2

The process procedure of Example 1 is repeated, except that now a glucose syrup is used as the polysaccharide material, having a water content of 20% by weight and a glucose content of also about 20%, the remainder consisting of oligo- or polysaccharide components. The raw materials used are listed according to quantity as follows:

256.3 kg of glucose syrup (20% H$_2$O, about 20% glucose)
795.0 kg of n-butanol
1397.0 kg of C$_{12/14}$ fatty alcohol
128.7 kg of additional, fully desalinated water (plus water from the glucose syrup 51.3 kg)
7.6 kg of p-toluene sulphonic acid×1 H$_2$O, of which
5.6 kg are in the first reactor, an additional
2.0 kg in the second reactor
4.2 kg of magnesium oxide The same procedure is used as described in Example 1. The reaction conditions used are as follows:
First reactor 145° C., 4.8 to 5.3 bar with a reaction time of 0.4 to 0.6 hours.
Second reactor 113° to 118° C., decreasing pressure from 700 to 10 m bar, reaction time 3 hours The reaction product worked up as in Example 1 corresponds in its appearance and nature to the alkylglucoside reaction product obtained from potato starch.

EXAMPLE 3

This example describes a laboratory mixture for the process according to the invention. The molar ratios for the reaction of starch: butanol: water: fatty alcohol were 1: 8: 6: 4, the quantity of starch being based on 1 mol of anhydroglucose, MW=162.

In the first step, the potato starch (93.5 g or 0.5 mol) containing 15% water was mixed with 296.5g (4 mol) of n-butanol, 39.7 g of water (a total of 3 mol with the water from the starch) and 1.6 g of p-toluene sulphonic acid and the mixture was stirred in an autoclave for half an hour at 145° C. (190 rpm). The pressure rose to 3.7 bar. After cooling to about 80 C the yellowish/brown clear reaction mixture was drawn off. In the second step, the fatty alcohol (388 g or 2 mol of dodecanol/tetradecanol in a weight ratio of 75:25) was placed together with 1.6 g of p-toluene sulphonic acid in a 1 liter 3-necked flask with stirrer, dropping funnel and distillation column with distillation bridge and the mixture was heated to 112° C. with stirring, After a vacuum of 15 mmHg had been applied, the product of step one at a temperature of about 80° C. was added within one and a half hours and at the same time a butanol/water mixture was distilled off. Then the vacuum was adjusted to 3 mmHg and the remaining butanol was drawn off over a period of about 1 hour. The reaction mixture was then cooled to about 90° C. and mixed with 2.0 g of magnesium oxide. Then the excess fatty alcohol was distilled off with stirring at 0.05 to 0.01 mmHg. The maximum sump temperature was 165° C. 334 g of fatty alcohol were obtained. The distillation residue was 136 g. The product thus obtained was converted at about 90° C. with water into an approximately 50% paste and bleached by the addition of 30% hydrogen peroxide solution (1% H$_2$O$_2$, based on the quantity of product). A yellowish mass was obtained which was colour-fast in an alkaline medium (colour numbers according to Klett, 5% solution in water/isopropyl alcohol 1:1, 1 cm dish, blue filter: 30 before and 40 after the alkali colour test).

We claim:

1. A process for preparing a reaction product containing surface active alkylglucoside compounds comprising a predominate content of alkyl monoglucoside from long chain monohydroxyl alcohols and a saccharide source selected from the group consisting of starch, polysaccharides other than starch, starch partial degradation products, and oligosaccharides other than starch partial degradation products, comprising formation of lower alkyl glucosides and transacetalization thereof with long chain monohydroxyl alcohols, which process comprises:

a) reacting the saccharide source under acidic catalysis with a sufficient amount of a mixture of water and lower alkanol, which mixture is in a single phase at the reaction conditions of a temperature above 100° C. and elevated pressure, to provide throughout the entire reaction a stoichiomeric excess of lower alkanol and a stirable and flowable reaction mixture and continuing the reaction until a liquid, virtually clear single-phase first reaction product is obtained;

b) admixing and reacting the first reaction product with a stoichiometric excess of the long chain alcohol heated to a reaction temperature above about 100° C., to form a second reaction mixture which is a single-phase at the operating temperature of the second reaction mixture throughout the entire reaction, under reaction conditions of pressure, temperature and rate of admixing that the water in the first reaction product is vaporized virtually immediately as it is admixed with the second reaction mixture; and c) evaporating the lower alkanol present in the first reaction product and formed by transacetalization to form a reaction product containing the surface active alkylglucoside compounds.

2. A process of claim 1, wherein the temperature of the second reaction mixture is maintained by indirect heat transfer with a heating medium at a temperature difference $\Delta T$ not greater than 30° C., wherein $\Delta T = T_{heating\ medium} - T_{second\ reaction\ mixture}$.

3. A process of claim 1, wherein at least a major portion of the heat energy required in the second reaction mixture is supplied by indirect heat transfer of a stream of the second reaction mixture circulated outside a main reaction zone.

4. A process of claim 1, wherein the first reaction mixture is heated by indirect heat transfer of a stream of the first reaction mixture outside of a main reaction zone.

5. A process of claim 1, wherein the lower alkanol comprises a C$_{3-5}$ monohydroxyl alcohol.

6. A process of claim 1, wherein the saccharide source comprises at least one member selected from the group consisting of powdered native starch, polyglucose and glucose syrup.

7. A process of claim 1, wherein step a) is carried out at a temperature above 125° C. and under a pressure of about 4 to 10 bar in a closed reaction zone.

8. A process of claim 1, wherein the second reaction step b) is carried out at temperatures below the temperature of reaction step a) under reduced pressure.

9. A process of claim 1, wherein transacetalization is carried out under an increasing vacuum.

10. A process of claim 1, wherein a further amount of acid catalyst is added to the second reaction mixture.

11. A process of claim 1, wherein the single phase mixture comprises water and butanol is substantially equal molar amounts.

12. A process of claim 1, wherein in step a) the molar ratio of saccharide source to water is in the range from about 1:5 to 1:12.

13. A process of claim 1, wherein in the second reaction mixture the molar ratio of starch, calculated as anhydroglucose, to the long chain alcohol ranges from 1:1.5 to 1:7.

14. A process of claim 1, wherein at the end of the reaction the acid catalyst is neutralized by addition of at least one basic compound selected from the group consisting of basic organic alkali metal compounds, basic organic alkaline earth metal compounds, basic organic aluminum compounds, basic inorganic alkali metal compounds, basic inorganic alkaline earth metal compounds and basic inorganic aluminum compounds to the second reaction mixture to a pH value of at least 8.

15. A process of claim 14, wherein the neutralized second reaction product is oxidatively bleached.

16. A process of claim 1, wherein the long chain monohydroxyl alcohol comprises compounds of natural or synthetic organic with chain lengths in the range from $C_{12-18}$.

17. A process of claim 2, wherein $\Delta T$ is not larger than 20° C..

18. A process of claim 5, wherein the monohydroxyl alkanol is n-butanol.

19. A process of claim 8, wherein the temperature is in the range of from 110° to 120°.

20. A process of claim 9, wherein the final pressure is about 10 m bar.

21. A process of claim 10, wherein the catalyst is a sulphonic acid.

22. A process of claim 13, wherein the molar ratio of starch, calculated as anhydroglucose, to the long chain alcohol is from 1:2.5 to 1:7.

23. A process of claim 21, wherein the molar ratio of starch, calculated as anhydroglucose, to the long chain alcohol is from 1:3 to 1:5.

24. A process of claim 15, wherein the neutralized second reaction product is oxidatively bleached with hydrogen peroxide.

25. A process of claim 15, wherein the neutralized second reaction mixture is oxidatively bleached with at least one member selected from the group consisting of peracids and peracid salts.

* * * * *